United States Patent [19]

Faryniarz et al.

[11] Patent Number: 5,135,747
[45] Date of Patent: Aug. 4, 1992

[54] DEODORANT/ANTIPERSPIRANT PRODUCTS WITH FRAGRANCE AND ENCAPSULATED ODOR COUNTERACTANT

[75] Inventors: Joseph R. Faryniarz, Oxford, Conn.; William K. Williams, Englewood, N.J.; Matthew Kuznitz, Branford, Conn.

[73] Assignee: Chesebrough-Pond's USA Co., Division of Conopco, Inc., Greenwich, Conn.

[21] Appl. No.: 702,794

[22] Filed: May 17, 1991

[51] Int. Cl.$^5$ .......................... A61K 7/32; A61K 7/46
[52] U.S. Cl. .................... 424/401; 424/76.4; 424/47; 424/78.03; 424/499; 424/59; 424/66; 424/67; 424/68; 512/4
[58] Field of Search .......... 424/65, 67, 68, 45, 424/47, 401, 76.1, 76.2, 76.4, 78.02, 78.03, 78.05; 512/4

[56] References Cited

U.S. PATENT DOCUMENTS

| | | | |
|---|---|---|---|
| 3,686,701 | 8/1972 | Charle et al. | 15/104.93 |
| 3,691,271 | 9/1972 | Charle et al. | 424/28 |
| 3,971,852 | 7/1976 | Brenner et al. | 426/103 |
| 4,226,889 | 10/1980 | Yuhas | 424/59 |
| 4,288,341 | 9/1981 | Hooper et al. | 252/107 |
| 4,289,641 | 9/1981 | Hooper et al. | 252/96 |
| 4,304,679 | 12/1981 | Hooper et al. | 252/106 |
| 4,322,308 | 3/1982 | Hooper et al. | 252/107 |
| 4,369,173 | 1/1983 | Causland et al. | 424/35 |
| 4,428,869 | 1/1984 | Munteanu et al. | 252/522 A |
| 4,504,465 | 3/1985 | Sampson et al. | 424/65 |
| 4,579,677 | 4/1986 | Hooper et al. | 252/95 |
| 4,617,185 | 10/1986 | DiPietro | 424/65 |
| 4,663,068 | 5/1987 | Hagemann et al. | 252/99 |
| 4,759,924 | 7/1988 | Luebbe et al. | 424/42 |
| 4,818,522 | 4/1989 | Ferentchak et al. | 424/66 |

FOREIGN PATENT DOCUMENTS

| | | |
|---|---|---|
| 1268423 | 9/1990 | Canada. |
| 437703 | 9/1971 | European Pat. Off. . |
| 0303461 | 2/1989 | European Pat. Off. . |
| 0404470 | 12/1990 | European Pat. Off. . |

OTHER PUBLICATIONS

"Encapsulated Perfumes in Aerosol Products", by Miles et al., J. Soc. Cosmet. Chem., 22, pp. 655-666 (Sep. 17, 1971).

Primary Examiner—Thurman K. Page
Assistant Examiner—Neil Levy
Attorney, Agent, or Firm—Milton L. Honig

[57] ABSTRACT

A malodor-reducing composition is provided for application to a human body. The composition includes an unscented malodor counteractant deoperfume mixture encapsulated within a semi-permeable wall material, a non-encapsulated fragrant perfume mixture imparting a distinct fragrance character, and a cosmetically acceptable vehicle.

3 Claims, No Drawings

DEODORANT/ANTIPERSPIRANT PRODUCTS WITH FRAGRANCE AND ENCAPSULATED ODOR COUNTERACTANT

BACKGROUND OF THE INVENTION

1. Field of the Invention

The invention is directed at a malodor-reducing composition for application to the human underarm

2. The Related Art

Antiperspirant and deodorant compositions generally contain a fragrance. Not only does the fragrance improve the aesthetic characteristics of the composition, but body malodor may also be masked by application of the pleasant smell. Of course, there is a limit in the level at which a masking fragrance can be applied. Too high levels can be offensive to a user.

One approach to the problem has been to release fragrance, deodorant and/or antiperspirant actives episodically in conjunction with generation of odor and/or sweat. Encapsulation of the actives is one method for accomplishing this objective.

Representative of the encapsulation technology is U.S. Pat. No. 4,369,173 (Causland et al) wherein aluminum chlorhydrate and other antiperspirant astringent salts are encapsulated within a hydrolyzed carbohydrate for use in antiperspirant consumer products.

Sanitary napkins are reported in U.S. Pat. No. 3,691,271 (Charle et al). A multiplicity of individual microcapsules are homogeneously distributed within the cellulose batting of the napkin. A deodorant lotion is described wherein a chlorinated compound, quaternary ammonium compound or other bacteriostat is enveloped within a microcapsule and the latter dispersed within a perfumed alcohol base.

U.S. Pat. No. 3,686,701 (Charle et al) describes cosmetic compositions for removing nail enamel containing rupturable microcapsules containing solvent and a perfume to mask the odor of the solvent.

Similar technology is reported in U.S. Pat. No. 3,971,852 (Brenner et al) which discloses perfume compositions within a polysaccharide matrix and an article by Miles et al, J. Soc. Cosmet. Chem., 22, pages 655–666 (Sept. 17, 1971) entitled "Encapsulated Perfumes in Aerosol Products". The Miles et al article discloses an apparently stable spray-dried encapsulated fragrance which may be formulated into aerosols. Therein is indicated that when sprayed on a surface under both in vivo and in vitro conditions, gradual fragrance release occurs upon exposure to moisture.

European Patent 437,703 (Suffis et al) emphasizes the importance of properly selecting wall material which will, upon contact with perspiration or other body fluids, release active ingredients in a controlled manner. Dextrins, gum arabic and polypeptides were suggested as suitable for encapsulating antibacterial compounds such as hexachlorophene. Perfumes are incorporated into most of the capsules and are even stated to be useful as the sole encapsulated deodorant.

An even more sophisticated approach is described in U.S. Pat. No. 4,428,869 (Munteaunu et al). Among the patent objectives is provision of a cologne containing a perfume characterized by an almost instantaneous aroma perception prior to use and when applied being effective over an extended period of time to deliver a controlled constant and continuous non-interrupted high impact fragrance release. The objective is accomplished through a combination of a non-confined fragrance in alcoholic solution which contains suspended therein an entrapped fragrance oil releasable either hydrolytically as a result of contact with excreted sweat or through mechanical rupture. Related technology is reported in Great Britain Application 87/19091 wherein a deodorant, antiperspirant or anticholinergic active substance is combined with a sensory response signal such as a fragrance or deodorant perfume combined within a capsule sensitive to skin moisture but resistant to extraction from alcohol present in a product delivery vehicle.

Several years ago fragrances were reported that when combined were found to provide the additional benefit of deodorancy. These perfumes were as a consequence dubbed "deoperfumes". See the disclosures in U.S. Pat. Nos. 4,288,341; 4,289,641; 4,304,679; 4,322,308; and 4,579,677 to Hooper et al and U.S. Pat. No. 4,663,068 to Hagemann et al.

More recently, there was reported in co-pending Application 07/539,638, abandoned, now continuing application 07806803, which draws priority from Great Britain Application 89/14055.2 (19 June 1989) that certain compositions of fragrance materials can confer deodorant effects in use even though they have in themselves a low or imperceptable level of fragrance (low odor intensity). These properties were said to be advantageous where an intense fragrance is not desired, while a deodorant effect was welcomed.

By way of background to the deodorant art, a variety of patents should be noted which disclose deodorant sticks structured with a polyhydric alcohol, soap, a bacteriostat and a fragrance. See, for instance, U.S. Pat. No. 4,759,924 (Luebbe et al), U.S. Pat. No. 4,617,185 (DiPietro) and U.S. Pat. No. 4,504,465 (Sampson et al), U.S. Pat. No. 4,226,889 (Yuhas) and Canadian Patent 1,268,423 (McCall). Indeed, U.S. Pat. No. 4,226,889 (Yuhas) has even specifically identified perfume stick products based upon stearate-water systems which may include specific natural products such as essential oils, flower oils, natural extracts well as animal mixtures such as ambergris and musk. These were said to generally fall into several well-known categories such as floral, spicy, woody, chyper or mossy, Oriental, herbal, leather-tobacco and aldehydic groups.

Although many advances have been made as shown above, there is considerable room for improving deodorant/antiperspirant products efficacy through manipulation of fragrances.

Accordingly, it is an object of the present invention to provide an antiperspirant and/or deodorant product which through a fragrance counteracts body odor over a prolonged period of use but without generating an overbearing fragrance concentration. Another object of the present invention is to provide an antiperspirant and/or deodorant product which is switched on under heavy perspiration but is re-encapsulated under dry conditions. A further object of the present invention is to provide an antiperspirant and/or deodorant product that can release an odor counteractant of virtually no fragrant character which would neutralize offending smells without masking and without leaving an extensive fragrance impression.

A still further object of the present invention is to provide an antiperspirant and/or deodorant product which avoids the necessity of a manufacturer being required to carefully formulate fragrance to compensate for topnotes being lost during application of the product or manufacture of the encapsulated fragrance.

These and other objects of the present invention will become more apparent by consideration of the following summary, detailed description and examples.

SUMMARY OF THE INVENTION

A malodor-reducing composition is provided for application to a human body comprising:

(i) a malodor counteractant mixture encapsulated within a semi-permeable wall material, said malodor counteractant having an Odor Intensity Index of less than 110 and meeting at least one deodorancy test selected from the group consisting of a Malodor Reduction Value Test and an Odor Reduction Value Test, each of which values must be at least 0.25;

(ii) a non-encapsulated fragrant perfume mixture present in an effective amount to impart a distinct odor character to said composition; and (iii) a cosmetically acceptable vehicle present in an effective amount to serve as a carrier for said fragrant perfume mixture and said encapsulated malodor counteractant.

DETAILED DESCRIPTION OF THE INVENTION

Now it has been discovered that a cosmetic composition may be formulated to meet the foregoing objectives by combining within the composition a normally fragrant perfume with an encapsulated, unscented deoperfume. The encapsulated, unscented deoperfume slowly releases its malodor counteractant over a period of time while the fragrant perfume provides a sensory impression.

It is to be understood that in the context of this invention the expression "unscented deoperfume" is defined as a composition whose odor intensity is considered to be imperceptable in use. On the other hand, the term, "perfume" or "fragrance", is intended to define a composition whose odor intensity is sufficiently significant that it may be perceptable in use.

Malodor counteractants of the present invention are believed to operate as olefactory blockers. These compounds may sterically hinder nose receptors from reacting with a malodor. Advantageously, at least about 25%, but preferably at least about 50% of the components in the counteractant mixture will have a vapor pressure below 0.05 mm at 20° C. and an odor intensity of at least 50%, preferably at least 75%, but optimally at least 90% less than n-butanol. On the other hand, the non-encapsulated perfume mixture of the present invention will release a fragrance intended to provide a pleasant smell. Advantageously, the non-encapsulated perfume mixture will have a vapor pressure of at least 0.05 mm at 20° C. with an odor intensity more than the odor intensity of the counteractant mixture.

Malodor counteractant mixtures of the present invention will meet at least one of the following criteria:

(a) an Odor Intensity Index of less than about 110, preferably less than about 105 and optimally less than about 100, when tested according to an Odor Intensity Test as described below, and (b) a Malodor Reduction Value of at least about 0.25, preferably at least about 0.5, when tested according to the test procedure set out in U.S. Pat. No. 4,663,068 or an Odor Reduction according to the test procedure set out in U.S. Pat. No. 4,304,679, both of which specifications are incorporated herein by reference.

A suitable selection of perfumery materials for incorporation into such compositions is for example provided in the Examples below. More generally, any of a wide range of perfumery materials may be incorporated into the compositions, provided that the basis of selection is such that it provides a deodorant effect, and the Odor Intensity Index of the resulting composition is as defined above.

Extensive directions for the selection of materials in order to provide a deodorant effect are given for example in U.S. Pat. No. 4,663,068 and U.S. Pat. No. 4,304,679.

It is helpful if the bulk of the individual ingredients chosen for the composition also individually possesses an Odor Intensity Index less than about 110, preferably less than about 100, or even lower. Small quantities of more intense materials may, however, be tolerated, e.g. for the purpose of adjusting the mild perfume note which may be given by the overall composition.

In a number of particular embodiments, the compositions can comprise at least 30% by weight of a musk, e.g. at least 35% or at least 40%. Where musks are present, either in these or in other amounts, they can usually be selected from musks such as galaxolide (TM) (IFF) (in Class 3 defined below) and/or Traseolide (TM) (Quest) (in Class 4 defined below).

Odor Intensity Index Method

The samples are assessed by a panel of a suitable number of assessors, e.g. about 34 who have been trained to score the intensity of a sample using the magnitude estimation technique. This is a ratio scaling method in which the relative intensity of each sample is scored in ratio to the intensities of a range of odor standards (here, benzyl acetate diluted in dipropylene glycol) at various concentrations.

An amount of 1.5 g ($\pm 0.1$ g) perfume, or 1.5 g ($\pm 0.1$ g) of benzyl acetate standard either neat or as a dilution in dipropylene glycol, is placed into a series of 7 ml white soda S.N.B. screw neck vials with 19 mm diameter necks. The samples are each coded and presented to the panel in a random order at least twice. A total of at least 64 assessments (or enough to reach statistical significance) is made for each sample by at least 16 panelists on each day over two days. Assessments are made in environmentally controlled assessment rooms using colored lighting to ensure that panelists are not influenced by any slight color differences between the samples.

Individual assessments are normalized and averaged to give a consensus intensity rating for each sample. The perceived intensities are expressed in arbitrary units and are derived from consensus magnitude estimates which are indicative of the ratio of perceived intensities, as follows:

Each panelist is required to assess the intensity of a control sample (10% benzyl acetate solution in dipropylene glycol) in addition to each test fragrance and the reference samples. The intensity value (magnitude estimate) of the control sample is then used to normalize all the other assessments for each panelist, as follows:

$$\text{Normalized Intensity} = \frac{\text{Intensity of Unknown}}{\text{Intensity of control}} \times 100$$

or:

-continued $$(I_N)_j = \frac{(i_K)_j}{(i_c)_j} \times 100$$

The normalized values for a sample are combined across all panelists to give a consensus value for the whole panel (the arithmetic mean).

$$\text{Odor Intensity Index} = \Sigma \frac{\text{(Normalized Panelist Ratings)}}{\text{Number of panelists}}$$

or:

$$I_K = \sum_1^J \frac{(I_N)_j}{J}$$

KEY
$I_K$ = odor intensity index for sample $k$ for the whole panel.
$(i_K)_j$ = odor intensity of sample (magnitude estimate) as reported by $j$'th panelist.
$(I_N)_j$ = single panelist's normalized datum.
$n$ = number of samples.
$J$ = number of panelists.
$K$ = sample number.
$(i_c)_j$ = odor intensity of control (magnitude estimate) as reported by $j$'th panelist.

The Malodor Reduction Value Test

A team of female assessors is selected for olfactory evaluation on the basis that each is able to rank correctly the odor levels of the series of aqueous isovaleric acid solutions listed in Table I and is able to detect the reduction in body odor following the application of personnel products to human axillae.

The panel consists of up to 42 female subjects who have been screened for body odor that is not unusually weak or strong or uneven between the axillae. Subjects are not chosen who include a lot of curry or garlic, etc. in their diet. New panelists are put on control samples for one week to allow this screening to take place. All panelists are routinely screened to ensure that they do not use antiperspirants and are supplied with a non-deodorant soap bar (Lux) for home use. They are also supplied with a placebo deodorant aerosol for used at home between tests and at weekends and are denied the use of any other underarm product. The panelists wear clothing of their own choice.

The test is run over the course of a week, i.e. Monday to Friday. On Monday afternoon the panelists are washed by a technician with unperfumed soap using a standard technique in which a wet flannel is soaped for 15 seconds, the axillae washed with the flannel for 30 seconds, then wiped with a water-rinsed flannel and dried with a paper towel. A separate flannel is used for each axilla.

The test products are then applied using a randomized design where each product is given a letter A, B, C, D, etc. which is unknown to the assessors. The deodorant stick is applied to the axilla using several strokes of the product. A balance is used to judge the weight loss of each stick so estimating the number of strokes needed to deliver the required dosage. A different product is worn in each axilla and is kept constant throughout the week of the test.

On Tuesday afternoon after 24 hours, the odor intensity of each axilla is evaluated. The assessors, operating without knowledge of the products used, will assign a score corresponding to the strength of odor on a scale of 0–5. Each assessor is unaware of the scores given by fellow assessors.

Before evaluation each panelist stands with their arms against their sides. They then raise their arms straight above their heads, flattening each axilla vault and making it possible for the assessor's nose to be brought close to the skin. the assessor evaluates the left and right axilla in turn. Panelists are then washed, as previously described, and the test products reapplied.

This routine of assessment, washing and reapplication is repeated on Wednesday and Thursday afternoon. On Friday afternoon the panelists are assessed but no further product applications are made. They may be washed if requested.

The scores from the four assessments are averaged for each assessor to give mean odor scores for each treatment over the week. These individual assessor scores are then averaged to give a team score. The results are analyzed via the computer which uses an Analysis of Variance routine. This takes into account the factors which lead to variability, e.g. subjects, days, left/right bias, etc. It also calculates the least significant difference figure at 95% confidence.

TABLE I

| Score | Odor Level | Conc. of Aqueous Isovaleric Acid (ml/l) |
|---|---|---|
| 0 | No odor | 0 |
| 1 | Slight | 0.013 |
| 2 | Definite | 0.053 |
| 3 | Moderate | 0.22 |
| 4 | Strong | 0.87 |
| 5 | Very Strong | 3.57 |

The average score of the "treated" (test) underarm is deducted from the average score of the "untreated" (control) underarm to give the Malodor Reduction Value of the malodor counteractant deoperfume mixture.

As a check that the selection of panel subjects is satisfactory for operation of the test, the average score with the control should be between 2.5 and 3.0.

Although the invention in its widest aspect provides malodor counteractant deoperfumes having a Malodor Reduction Value of from 0.25 to 3.0, preferred malodor counteractant mixtures are those which have a Malodor Reduction Value of at least 0.30, preferably at least 0.50, optimally at least 1.00. The higher the minimum value, the more effective is the malodor counteractant mixture as a deodorant as recorded by the assessors in the Malodor Reduction Value Test. It has also been noted that consumers, who are not trained assessors, can detect by self-assessment a noticeable reduction in malodor where the Malodor Reduction Value is at least 0.30, the higher the Malodor Reduction Value above this figure, the more noticeable is the deodorant effect.

Classification of Malodor Counteractant Deoperfume Mixture Components

Components of the malodor counteractant mixture will be classified into six chemically defined classes. However, before defining this classification in greater detail, it is necessary first to clarify some of the terms that will be employed in assigning certain of the deoperfume components to a chemical class. This is done first by describing the components in terms of four categories, each of which is given below together with examples of components which are to be assigned to each category.

(1) Single chemical compounds whether natural or synthetic, for example, iso-eugenol: the majority of components are in this category.

(2) Synthetic reaction products (products of reaction), mixtures of isomers and possible homologues, for example, alpha-iso-methyl ionone.

(3) Natural oils and extracts, for example, clove leaf oil.

(4) Synthetic oils: this category includes materials that are not strict analogues of natural oils but are materials that result from attempts to copy or improve upon certain natural oils, for example Bergamot AB 430 and Geranium AB 76.

Components of Categories (3) and (4), although often uncharacterized chemically, are available commercially.

Where a material is supplied or used conventionally for convenience as a mixture, e.g., p-t-amyl cyclohexanone diluted with diethyl phthalate, for the purposes of this specification two components are present, so that use of 5% of a blend of 1 part of this ketone and 9 parts of diethylphthalate is represented as 0.5% of the ketone and 4.5% of diethylphthalate.

It has been found advantageous in formulating the most effective malodor counteractant mixtures to use components that satisfy the conditions of:

(i) at least five different components being present;

(ii) at least four different chemical classes (to be defined below) being represented;

(iii) at least 50, preferably at least 55% and most preferably from 60 to 100% by weight of the malodor counteractant mixture comprising components conforming with the classification below;

(iv) not considering a component contributing to the efficacy of the malodor counteractant mixture if it is present in a concentration of less than 0.5% by weight.

Each component should be allocated to one of six classes. These classes are:

Class 1 -- Phenolic substances;
Class 2 -- Essential oils, extracts, resins and synthetic oils (denoted "AB");
Class 3 -- Aldehyde and ketones;
Class 4 -- Nitrogen-containing compounds;
Class 5 -- Esters;
Class 6 -- Alcohols and ethers.

In assigning a component to a class, the following rules are to be observed. Where the component could be assigned to more than one class, the component is allocated to the class occurring first (lowest number) in the order given above; for example methyl anthranilate, which is a nitrogen-containing compound, is placed in Class 4, although as an ester it otherwise might have been allocated to Class 5. Similarly, ethyl salicylate, which is phenolic in character, is allocated to Class 1 instead of Class 5.

The nomenclature adopted for the components listed below and for the deoperfume ingredients which appear in the Example formulations is, so far as is possible, that employed by Steffan Arctander in "Perfume and Flavor Chemicals (Armona Chemicals)" Volume I and II (1969) and the "Perfume & Flavor Materials of Natural Origin" (1960) by the same author. Where a component or ingredient is not described by Arctander, then either the chemical name is given or, where this is not known the perfumery house specialty code name is given. Note that synthetic oils denoted "AB" are available from Quest International Limited.

Class 1 - Phenolic Substances iso-Amyl salicylate
Carvacrol
Clove leaf oil
Ethyl salicylate
iso-Eugenol
Hexyl salicylate
Thyme oil red Class 2 - Essential Oils, Extracts, Resins and Synthetic Oils (denoted "AB")

Bergamot AB 430
Geranium AB 76
Rose AB 380
Rose AB 409

Class 3 - Aldehydes and Ketones

6-Acetyl-1,1,3,4,4,6-hexamethyl-tetrahydronaphthalene
p-t-Amyl cyclohexanone
2-n-Heptylcyclo-pentanone
α-iso-Methyl ionone
β-Methyl naphthyl ketone Class 4 - Nitrogen-containing Compounds iso-Butyl quinoline
Methyl anthranilate Class 5 Esters o-t Butylcyclohexyl acetate
Diethyl phthalate
Nonanediol-1,3-diacetate
Nonanolide-1,4
i-Nonyl acetate
i-Nonyl formate
Phenylethyl phenyl acetate Class 6 - Alcohols & Ethers Cinnamic alcohol
Dimyrcetol
1,3,4,6,7,8-Hexahydro-4,6,6,7,8, 8-hexamethyl cyclopenta-a-2-benzopyran
Hydroxymethyl isopropyl cyclopentane
3a-Methyl-dodecahydro-6,6,9a-trimethylnaphtho-2(2,1-b)furan
Tetrahydromuguol Likewise, it has been stated that at least four different classes of components should be represented in the malodor counteractant deoperfume mixture. Superior unscented deoperfumes can, however, be obtained if more than four classes are represented. Accordingly, preferably five or all six classes can be represented in the malodor counteractant mixture.

It has been shown by the preparation, examination and testing of many malodor counteractant mixtures that the best results are obtained by keeping within the aforementioned rules. For example, mixtures which contain less than the minimum concentration of components of 50% are unlikely to result in a deoperfume which has sufficient deodorant property expressed in terms of its Malodor Reduction Value as hereinafter defined.

It should be explained that components in the malodor counteractant mixture present for purposes other than obtaining a deodorant effect, e.g. to serve as an adjunct, are excluded from the operation of the preceding instructions to the extent that the component is required for that other purpose. Levels at which adjuncts are conventionally present in perfumes or in products to which perfumes are added is well-established for conventional materials and readily determinable for new materials so that the application of the above exclusion presents no difficulty.

Encapsulation

A wide variety of materials may serve as the encapsulation polymeric substances. Among the synthetic polymeric substances may be included polyethylene waxes, polyvinyl acetate, polyvinyl pyrrolidine, polyamides, polyesters, and homo- and co-polymers formed from monomers selected from the group consisting of acrylic, methacrylic, maleic, fumaric, itaconic acids and their esters and salts. Among suitable natural substances may be included polysaccharides, gelatin, gum acacia and arabic, carboxymethyl cellulose, hydroxyalkyl cellulose, alkyl cellulose and natural waxes.

Most preferred are the polysaccharides, especially the modified starches and dextrins of low viscosity which include maltodextrins.

A particularly preferred example of the modified starches is Purity Gum BE which is a cornstarch which has been treated with succinic anhydride. Somewhat less preferred, although still suitable, is a maltodextrin known as Encapsul 855. Both of the aforementioned materials are available from the National Starch and Chemical Company.

Encapsulating matrix may form anywhere from about 10 to about 90%, preferably about 30 to about 75%, optimally between about 40 and 65% by weight of the capsule. The malodor counteractant mixture will be incorporated within the capsule at levels from about 10% to about 90%, preferably from about 30 to about 75% by weight of the capsule.

Average particle size of the capsule normally will range from about .1 to about 150 $\mu$m, preferably between from about 5 and 50 $\mu$m.

A variety of techniques may be used to form the capsules. For instance, moisture-sensitive capsules can be formed by preparing an emulsion of water, the encapsulating matrix and the malodor counteractant deoperfume mixture, together with any other materials dissolved or dispersed therein which are required to be included in the capsules. The emulsion is then spray-dried according to conventional technology to form the capsules containing the deoperfume mixture. Encapsulated malodor counteractant mixtures of this invention will normally be incorporated into compositions in amounts ranging anywhere from about 0.05 to 5% by weight, preferably between 0.2 and about 2%, optimally between 0.25 and 0.8% by weight.

Vehicles

A broad range of vehicles for carrying the capsules and unencapsulated fragrance perfume may be suitable for the present invention. The vehicle may either be a liquid, a solid or an aerosol. Amounts of the vehicle may range anywhere from about to about 99.8%, preferably from about 80 to about 99%, optimally between about 95 and 99% by weight of the total composition.

Liquid carriers may include both hydrophilic and hydrophobic fluids. Among possible hydrophilic fluids are water, $C_1$-$C_4$ alkanols, $C_2$-$C_4$ polyhydroxyalkanols and combinations thereof. Examples of the latter materials are ethanol, isopropanol, ethylene glycol and propylene glycol. Hydrophobic fluids may include butane, pentane, hexane and other light hydrocarbons, halocarbons, esters and ketones. For example, suitable for purposes of this invention are ethyl acetate, acetone and methyl ethyl ketone.

Solids suitable as vehicles for the present invention are particularly exemplified by soap and solid aqueous gels structured by such materials as soap, cross-linked polyacrylates (e.g. Carbopol®), fatty acids such as stearic acid and polyhydricylic compounds such as polyethylene glycol, dibenzol sorbitol and solid waxes.

Optional Active Ingredients

Compositions of the present invention may include a wide variety of Active Ingredients. These ingredients may include bacteriostats, astringent salts, anticholinergics, emollients and sunscreen agents. Amounts of these active ingredients may range anywhere from about 0.1 to about 50% by weight of the composition, depending upon the specific type of Active Ingredient. For instance, the amounts of deodorant astringent salts and anticholinergics will preferably range anywhere from about 0.3 to about 5%, preferably from about 0.5 to about 1% by weight of the composition. On the other hand, emollients may range preferably from about 5 to about 30% by weight of the composition.

Suitable deodorants include any compound, other than the malodor counteractants, that may function to reduce the level of or eliminate microflora on the skin surface. Specific examples are 2,4,4'-trichloro-2'-hydroxydiphenyl ether (also known as Irgasan DP300 or Triclosan), cetyltrimethylammonium bromide, cetylpyridinium chloride, benzethonium chloride, di-isobutyl phenoxethoxyethyl dimethylbenzylammonium chloride, N-alkylpyridinium chloride, N-cetylpyridinium bromide, sodium-N-lauroyl sarcosine, zinc phenyl sulphonate, farnesol and ethyl lactate. Precursors of deodorants other than deoperfume can also be employed.

Astringent salts also known as antiperspirant actives are compounds that function to reduce or eliminate the appearance of perspiration at the skin surface. Examples of such actives include aluminum chloride, aluminum sulphate, aluminum chlorohydrate; basic aluminum bromide, zirconyl chloride, zirconyl hydroxide, zirconyl chlorohydrate and complexes thereof with an amino acid, such as glycine, and mixtures of two or more of the above. Most preferred are aluminium zirconium chlorohydrate complexes, especially these complexes with glycine.

Anticholinergics are substances which function to reduce or eliminate the generation of perspiration before it reaches the skin surface. Examples of such substances are scopolamine derivatives, such as scopolamine hydrobromide and esters thereof, such as benzyl scopolamine hydrobromide.

Emollients may include synthetic esters such as isopropylmyristate, silicone oils, mineral oils and vegetable oils all of which give rise to a tactile response in the form of an increase in skin lubricity.

The following examples will more fully illustrate the embodiments of this invention. All parts, percentages and proportions referred to herein and in the appended claims are by weight of the total composition unless otherwise stated.

EXAMPLE 1

A capsule is prepared by forming an emulsion of Purity Gum BE (28 parts), a malodor counteractant deoperfume mixture (7 parts) and water (65 parts). The mixture is then agitated and spray-dried in a dryer utilizing about 200 c.f.m. of air with an outlet temperature of about 200° F.

The malodor counteractant deoperfume utilized has an Odor Intensity Index of 87 and contains the following components:

| Component | Weight % |
| --- | --- |
| Cedar Wood Oil (Virginian) | 2.0 |
| Cinnamic Alcohol | 2.0 |
| Diethyl Phthalate | 13.0 |
| Galaxolide DEP (50:50 mixture with diethyl phthalate) | 5.0 |
| Geranyl Phenylacetate | 4.0 |
| Guaiacwood Oil (rectified) | 1.0 |
| Linalyl Benzoate | 4.0 |
| Moss Base AB 7004 (*) | 6.0 |
| Phenylethyl Phenylacetate | 3.0 |
| Rose Base AB 7003 (*) | 20.0 |
| Traseolide (*) | 40.0 |
| | 100.0 |

(*)Available from Quest International

The odor type of this formulation is mildly floral, mossy, rose, and musk.

The resultant capsules are then made into an antiperspirant composition of the following formula:

| Antiperspirant Stick | |
| --- | --- |
| Ingredient | Weight % |
| Dow 245 Fluid (silicone) | q.s |
| Stearyl Alcohol | 16 |
| Castor Wax | 3 |
| Talc | 5 |
| Aluminum Zirconium Tetrachlorhydrate | 20 |
| Fragrant Perfume (unencapsulated) | 1 |
| Capsules (see above) | 1 |

The unencapsulated fragrant perfume has components as outlined in the table below.

| Fragrance Components | Weight % |
| --- | --- |
| Phenyl ethyl alcohol | 13.00 |
| Dihydromyrcenol | 5.00 |
| Linalool | 8.00 |
| Bergamot oil | 5.00 |
| Galaxolide IPM | 10.00 |
| Isolongifolanone | 5.00 |
| alpha-Methyl ionone Iso | 5.00 |
| Lyral (cycloaliphatic aldehyde) | 4.00 |
| Hexyl cinnamic aldehyde ($\alpha$-$\beta$-unsaturated aldehyde) | 6.00 |
| Linalyl acetate | 3.00 |
| Citronellyl acetate | 5.00 |
| Phenyl ethyl acetate | 6.00 |
| Acetyl tributyl citrate | 25.00 |

EXAMPLE 2

The malodor counteractant deoperfume utilized has an Odor Intensity Index of 85 and contains the following components:

| Component | Weight % |
| --- | --- |
| Benzyl Alcohol | 8.0 |
| Benzyl Salicylate | 7.5 |
| Cedar Wood Oil (Virginian) | 2.0 |
| Galaxolide DEP | 20.0 |
| Grisalva (10% solution in dipropylene glycol) (IFF) | 1.0 |
| Hercolyn D (Hercules) | 5.0 |
| Isobutyl Benzoate | 3.0 |
| Isobutyl Cinnamate | 2.0 |
| Linalyl Cinnamate | 1.0 |
| Moss Base AB 7004 (*) | 5.0 |
| Muguet Base AB 7001 (*) | 20.0 |
| Tonalid (7-acetyl-1,1,3,4,4,6-hexamethyl-tetrahydronaphthalene) (Polak's Frutal Works) | 5.0 |
| Traseolide (*) | 20.0 |
| | 100.0 |

(*) Available from Quest International

The odor type of this formulation is mildly woody, mossy, muguet and musk.

Capsules containing the above unscented deoperfume are prepared according to Example 1. These capsules are then incorporated into an aerosol antiperspirant product described as follows:

| Aerosol Antiperspirant | |
| --- | --- |
| Ingredient | Weight % |
| Absolute Ethanol | 15 |
| Activated Aluminium Chlorydrate (astringent salt) | 4 |
| Bentone 38 | 1.5 |
| Capsules (see above) | 1 |
| Fragrant Perfume (unencapsulated) | 1 |
| S-31 Hydrocarbon | 77.5 |

The unencapsulated fragrant perfume has components as outlined in the table below.

| Component | (Wt. %) |
| --- | --- |
| Benzyl salicylate | 6.00 |
| Coumarin | 4.00 |
| Phenyl ethyl alcohol | 10.00 |
| Lilial (aryl substituted aldehyde) | 5.00 |
| alpha-Methyl ionone Iso | 3.00 |
| Para-t-butyl cyclohexyl acetate | 6.00 |
| Dihydromyrcenol | 12.00 |
| Acetyl cedrene | 6.00 |
| Allyl amyl glycolate | 1.00 |
| Galaxolide IPM | 5.00 |
| Vanillin | 3.00 |
| Hexyl cinnamic aldehyde | 5.00 |
| Patchouli oil | 5.00 |
| Bergamot oil | 10.00 |
| Citronellol | 10.00 |
| Carbitol | 7.00 |

EXAMPLE 3

The malodor counteractant perfume utilized has an Odor Intensity Index of 72 and contains the following components:

| Component | Weight % |
| --- | --- |
| Benzyl Alcohol | 5.0 |
| Benzyl Cinnamate | 4.0 |
| Benzyl Salicylate | 20.0 |
| Cinnamyl Cinnamate | 1.0 |
| Diethyl Phthalate | 5.0 |
| Galaxolide DEP | 8.0 |
| Jasmin AB 7002 (*) | 20.0 |
| Linalyl Cinnamate | 5.0 |
| Sandalone AC 802 (*) | 2.0 |
| Traseolide (*) | 30.0 |
| | 100.0 |

(*) Available from Quest International

The odor type of this formulation is mildly sweet, floral and musk.

Capsules containing the above unscented deoperfume are prepared according to Example 1. These capsules are then incorporated into a roll-on lotion product described as follows:

| Roll-on Lotion | |
|---|---|
| Ingredient | Weight % |
| Dow 344 (silicone) | q.s |
| Bentone 38 | 3.5 |
| Ethanol (190 Proof) | 2.0 |
| Aluminum Zirconium Tetrachlorhydrate | 20.0 |
| Capsules (see above) | 1.0 |
| Fragrant Perfume (unencapsulated) | 1.0 |

The unencapsulated fragrant perfume has components as outlined in the table below.

| Component | Weight % |
|---|---|
| Phenyl ethyl alcohol | 15.00 |
| Dihydromyrcenol | 8.00 |
| alpha-Methyl ionone Iso | 6.00 |
| Bergamot oil | 5.00 |
| Benzyl salicylate | 3.00 |
| Styrallyl acetate | 3.00 |
| Hedione | 5.00 |
| Lavindin oil abrialis | 10.00 |
| Lyral (cycloaliphatic aldehyde) | 1.00 |
| Pathouly oil | 8.00 |
| Lemon oil | 10.00 |
| Galoxolide DEP | 16.00 |
| Linalool | 5.00 |
| Acetyl cedrene | 5.00 |

The foregoing description and Examples illustrate selected embodiments of the present invention. In light thereof, various modifications will be suggested to one skilled in the art all of which are within the spirit and purview of this invention.

What is claimed is:

1. A malodor-reducing composition for application to a human body comprising:
   (i) a malodor counteractant mixture encapsulated within a semipermeable wall material, said malodor counteractant having an Odor Intensity Index of less than 110 and meeting at least one deodorancy test selected from the group consisting of a Malodor Reduction Value Test and an Odor Reduction Value Test, each of which values must be at least 0.25, said malodor counteractant mixture having at least 25% by weight of the mixture exhibiting a vapor pressure below 0.05 mm at 20° C. and an Odor Intensity of at least 50% less than n-butanol, and said malodor counteractant mixture having components allocated to one of 6 classes consisting of:

Class 1 -- Phenolic substances
   Class 2 -- Essential oils, extracts, resins and synthetic oils
   Class 3 -- Aldehyde and ketones
   Class 4 -- Nitrogen-containing compounds
   Class 5 -- Esters
   Class 6 -- Alcohols and ethers provided that where said malodor counteractant mixture component could be assigned to more than one class, said component is allocated to the class occurring first in the order given above; said components being so selected that:
   (a) the mixture contains at least five different components;
   (b) said mixture contains components from at least four of the six classes; and
   (c) any component present in said mixture at a concentration of less than 0.5% by weight of said mixture is eliminated from any requirements of (a) and (b);
   (ii) a nonencapsulated fragrant perfume mixture present in an effective amount to impart a distinct odor character to said composition, said nonencapsulated fragrant perfume mixture having a vapor pressure of at least 0.05 mm at 20° C. with an Odor Intensity more than that of said malodor counteractant mixture; and
   (iii) a cosmetically acceptable vehicle present in an effective amount to serve as a carrier for said fragrant perfume mixture and said encapsulated malodor counteractant.

2. The composition according to claim 1 wherein said malodor counteractant mixture has at least about 50% by weight of the mixture exhibiting a vapor pressure below 0.05 mm at 20° C. and an Odor Intensity of at least 90% less than a n-butanol.

3. The composition according to claim 1 further comprising an Active Ingredient selected from a group consisting of bacteriostats, astringent salts, anticholinergics and emollients.

* * * * *